United States Patent [19]

Potthoff-Karl et al.

[11] Patent Number: 5,196,188

[45] Date of Patent: Mar. 23, 1993

[54] TERPOLYMERS, USE THEREOF IN HAIR SETTING COMPOSITIONS FOR INCREASED STIFFNESS, AND HAIR SETTING COMPOSITIONS CONTAINING SAME

[75] Inventors: Birgit Potthoff-Karl, Ludwigshafen; Karin Sperling-Vietmeier, Neustadt; Franz Frosch, Bad Durkheim; Axel Sanner, Frankenthal, all of Fed. Rep. of Germany

[73] Assignee: BASF Aktiengesellschaft, Ludwigshafen, Fed. Rep. of Germany

[21] Appl. No.: 763,417

[22] Filed: Sep. 20, 1991

[30] Foreign Application Priority Data

Oct. 8, 1990 [DE] Fed. Rep. of Germany ....... 4031912

[51] Int. Cl.⁵ ............................................. A61K 7/11
[52] U.S. Cl. ..................................... 424/71; 424/70; 424/47; 424/DIG. 1; 424/DIG. 2
[58] Field of Search ............... 424/71, 47, DIG. 2, 424/DIG. 1; 524/548; 525/326.9; 526/264

[56] References Cited

U.S. PATENT DOCUMENTS

| | | | |
|---|---|---|---|
| 3,405,084 | 10/1968 | Bobac et al. | 424/DIG. 1 |
| 3,577,517 | 5/1971 | Kubot et al. | 424/DIG. 1 |
| 3,634,436 | 1/1972 | Palmer | 424/47 |
| 3,692,893 | 9/1972 | Palmer | 424/47 |
| 4,767,613 | 8/1988 | Nuber et al. | 424/71 |

FOREIGN PATENT DOCUMENTS 0000161 1/1979 European Pat. Off. .
0257444 3/1988 European Pat. Off. .

Primary Examiner—Thurman K. Page
Assistant Examiner—D. Colucci
Attorney, Agent, or Firm—Oblon, Spivak, McClelland, Maier & Neustadt

[57] ABSTRACT

A terpolymer suitable for use as a film former in hair setting compositions is obtainable by free radical polymerization of 10%–24% by weight of N-vinylpyrrolidone, 46%–74% by weight of tert-butyl acrylate or methacrylate and 16%–30% by weight of acrylic or methacrylic acid, whose carboxyl groups may be partially or completely neutralized with an organic amine, ammonia or a basic alkali metal compound and which has a K value of from 25 to 65.

9 Claims, No Drawings

TERPOLYMERS, USE THEREOF IN HAIR SETTING COMPOSITIONS FOR INCREASED STIFFNESS, AND HAIR SETTING COMPOSITIONS CONTAINING SAME

The present invention relates to a terpolymer which is obtainable by free radical polymerization of 10-24% by weight of N-vinylpyrrolidone, 46-74% by weight of tert-butyl acrylate or methacrylate and 16-30% by weight of acrylic or methacrylic acid, whose carboxyl groups may be partially or completely neutralized with an organic amine, ammonia or a basic alkali metal compound and which has a K value of from 25 to 65.

The present invention further relates to the use of these terpolymers in hair setting compositions for increased stiffness and to hair setting compositions containing same U.S. Pat. No. 3,405,084 (1) describes neutralized terpolymers for hair spray formulations, which consist of from 25 to 75% by weight of N-vinylpyrrolidone, from 20 to 70% by weight of an alkyl ester of acrylic or methacrylic acid with a straight-chain or branched radical of from 1 to 10 carbon atoms in the ester alcohol and from 3 to 25% by weight of acrylic or methacrylic acid.

EP-A-257 444 (2) concerns a terpolymer for hair treatment compositions, which is obtained by free radical polymerization of from 20 to 50% by weight of N-vinylpyrrolidone, from 40 to 70% by weight of tert-butyl acrylate or methacrylate and from 2 to 15% by weight of acrylic or methacrylic acid, whose carboxyl groups may be neutralized with an organic amine to an extent of from 5 to 100% and which has a K value of from 10 to 60.

In recent years, film formers for hair treatment and hair setting compositions have increasingly been rated not just according to the criteria of curl retention and compatibility with apolar propellants such as hydrocarbons and dimethyl ether but also in respect of water-solubility and in particular the washoff properties and stiffening effect, since the trend is away from traditional water-free hair spray formulations and toward aqueous formulations with little, if any, propellant. Good washoff characteristics are desirable for example because even low residual levels of polymer in the hair lead to problems with the restyling of the hair. It is known of the compositions of (2) that as the K value, which can be considered a measure of the stiffening effect, increases the washoff characteristics of the film-forming polymer in the hair and the water-solubility of the polymer in the formulations deteriorate dramatically at the same time.

It is an object of the present invention to provide a polymer for hair products which while giving the same order of curl retention and propane/butane compatibility values and while forming films on the hair of little, if any, stickiness exhibits an increased stiffening effect coupled with good washoff characteristics and water-solubility.

We have found that this object is achieved by the terpolymer defined at the beginning, which, compared with the compositions of (2), has higher K values but at the same time is readily washed off and is sufficiently water-soluble.

In a preferred embodiment, the terpolymer of the present invention is formed from 10-20% by weight of N-vinylpyrrolidone, 55-74% by weight of tert-butyl acrylate or methacrylate and 16-25% by weight of acrylic or methacrylic acid.

The terpolymers of the present invention are advantageously prepared by free radical polymerization under conventional conditions. The customary techniques are employed, for example the methods of suspension, emulsion or solution polymerization.

A particularly advantageous choice is solution polymerization in an organic solvent, generally an alcohol. The polymerization is customarily carried out at from 60° to 160° C., at atmospheric pressure or under autogenous pressure.

To obtain particularly low residual monomer contents, it is of advantage as per EP-B-000 161 (3) to add to the reaction mixture, after the main polymerization has ended, from 0.05 to 0.5% by weight, based on the monomers used, of di-tert-butyl peroxide, di-tert-amyl peroxide, dicumyl peroxide, 2,5-dimethyl-2,5-bis(tert-butylperoxy)hexane, 2,2-bis(tert-butylperoxy)butane, 1,1-bis(tert-butylperoxy)-3,3,5-trimethylcyclohexane or 4,4-di(tert-butylperoxy)butyl valerate and to carry out the postpolymerization at a higher temperature than the main polymerization, within the range from 100 to 200° C.

The initiators used for the free radical polymerization reaction are the customary peroxo or azo compounds, for example diacyl peroxides, e.g. dibenzoyl peroxide, peroxyesters, e.g. tert-butyl perpivalate or tert-butyl per-2-ethylhexanoate, dialkyl peroxides, e.g. di-tert-butyl peroxide or 2,5-dimethyl-2,5-di(tert-butylperoxy)-hexane, alkyl hydroperoxides, e.g. tert-butyl hydroperoxide, or azo compounds, e.g. azobisisobutyronitrile or methyl azobisisobutyrate, advantageously in amounts of from 0.1 to 2% by weight, based on the weight of the monomers.

The amounts of monomer and solvent are advantageously chosen in such a way as to produce 30-80% strength by weight solutions of the terpolymers. Any organic solvent in the solution can be removed in a conventional manner, for example by distillation, and be replaced by water if a waterborne hair setting composition is desired. If necessary, the solvent can also be completely removed in a conventional manner, for example by spray drying.

The terpolymers of the present invention are preferably partially or completely neutralized with organic amines, ammonia and/or basic alkali metal compounds, the degree of neutralization of the carboxyl groups ranging from 5 to 100%. Particularly preferably the degree of neutralization of the carboxyl groups is from 50 to 100%, in particular from 70 to 100%.

If the carboxyl groups are to be neutralized with an organic amine, they are preferably neutralized with an alkanolamine from the series of the mono-, di- or trialkanolamines having from 2 to 5 carbon atoms in the alkanol moiety, such as mono-, di- or triethanolamine, mono-, di- or tripropanolamine or 2-amino-2-methylpropanol, or alkanediolamines having from 2 to 4 carbon atoms in the alkanediol moiety such as 2-amino-2-methyl-1,3-propanediol or 2-amino-2-ethyl-1,3-propanediol, or with di(methoxyethyl)amine or with primary, secondary or tertiary alkylamines having in total from 5 to 10 carbon atoms, such as N,N-diethylpropylamine. Of these, 2-amino-2-methylpropanol, triisopropanolamine and 2-amino-2-ethyl-1,3-propanediol are preferred.

The carboxyl groups may further be neutralized with ammonia or with basic alkali metal compounds such as alkali metal hydroxides, e.g. lithium hydroxide, or in particular sodium hydroxide or potassium hydroxide, alkali metal carbonates, e.g. sodium carbonate or potassium carbonate, or alkali metal alcoholates, e.g. sodium methoxide or ethoxide. It is also possible to use mixtures of organic amines, ammonia and basic alkali metal compounds.

The terpolymers of the present invention have K values of from 25 to 65, preferably from 35 to 55, measured in 1% strength by weight solution in ethanol at 25° C. in the acid form. The K value is a measure of molecular weight (Fikentscher, Cellulosechemie 13 (1932), 58-64, 71-74). The K value can in principle be set via the polymerization conditions.

The terpolymers of the present invention are highly suitable for use as film formers in hair setting compositions. Such hair setting compositions therefore also form part of the subject-matter of the present invention. They are employed for example in the form of lotions, mousses, gels or sprays.

The hair setting compositions of the present invention preferably contain from 1 to 15% by weight, in particular from 2 to 10% by weight, of a terpolymer of the present invention, from 10 to 99% by weight of a solvent selected from the group consisting of water, acetone, ethanol, n-propanol, n-butanol, isopropanol, 1-methoxypropanol and mixtures thereof, the use of water, ethanol and isopropanol being particularly advantageous, and from 0 to 90% by weight of a propellant selected from the group consisting of propane, n-butane, isobutane, 2,2-dimethylpropane, isopentane, dimethyl ether and mixtures thereof, the use of propane and n-butane and a mixture thereof, for example in the weight ratio of 40:60 or 25:75, being particularly advantageous.

Other customary ingredients, such as scents, preservatives and others, may be present in their customary amounts.

An advantageous formulation of a hair setting lotion contains for example:

from 1 to 15% by weight of a terpolymer of the present invention whose carboxyl groups have been neutralized to a degree of from 5 to 100%, preferably from 50 to 100%, from 0 to 99% by weight of a solvent selected from the group consisting of acetone, ethanol, propanol, n-butanol, isopropanol, 1-methoxy-2-propanol and mixtures thereof, and from 0 to 99% by weight of water.

A preferred composition for a hair setting lotion is predominantly aqueous and contains from 2 to 10% by weight of the terpolymer and from 60 to 98% by weight of water and optionally, as remainder to 100% by weight, one of the abovementioned solvents or mixtures thereof.

An advantageous and convenient composition for hair mousses has the following recipe:

from 1 to 15% by weight, preferably from 5 to 10% by weight, of a terpolymer of the present invention whose carboxyl groups have been neutralized to a degree of from 5 to 100%, preferably from 50 to a 100%, from 5 to 90% by weight, preferably from 60 to 80% by weight, of water, from 0 to 15% by weight, preferably from 5 to 10% by weight, of a solvent selected from the group consisting of acetone, ethanol, n-propanol, n-butanol, isopropanol, 1-methoxy-2-propanol and mixtures thereof, and from 50 to 20% by weight of a propellant selected from the group consisting of propane, n-butane, isobutane, 2,2-dimethylpropane, isopentane, dimethyl ether and mixtures thereof, mixtures of propane/butane being preferred.

Conventional mousse formation and mousse stabilization assistants are added to these compositions in an amount of from 0.5 to 1% by weight, based on the total weight.

An advantageous hair spray composition contains for example:

from 1 to 15% by weight of a terpolymer of the present invention whose carboxyl groups have been neutralized to a degree of from 5 to 100%, preferably from 50 to 100%, from 10 to 95% by weight of a solvent selected from the group consisting of acetone, ethanol, n-propanol, n-butanol, isopropanol, 1-methoxy-2-propanol and mixtures thereof, and from 5 to 90% by weight of a propellant selected from the group consisting of propane, n-butane, isobutane, 2,2-dimethylpropane, isopentane, dimethyl ether and mixtures thereof.

The customary constituents and compositions of other hair setting products are known to those skilled in the art and consequently need not be explained here at length.

The terpolymers of the present invention have an excellent stiffening effect if used as film formers in hair setting compositions, but they are also readily washed out of the hair and are sufficiently water-soluble in hair care formulations. The formulations are in general from clear to opaque. Furthermore, the terpolymers of the present invention do not sticky the hair, and their curl retention and propane/butane compatibility values are adequate for practical use and of the same order of magnitude a those of comparable prior art film formers.

EXAMPLE 1

Preparation of a terpolymer of 20% by weight of N-vinylpyrrolidone, 60% by weight of tert-butyl acrylate and 20% by weight of methacrylic acid 20 g of N-vinylpyrrolidone, 60 g of tert-butyl acrylate and 20 g of methacrylic acid are dissolved in 24 g of ethanol. A stirred flask equipped with a reflux condenser and 2 dropping funnels was charged with 10% of this monomer solution, 10% of a prepared initiator solution of 0.8 g of tert-butyl perpivalate in 27 g of ethanol, and 50 g of ethanol, and the mixture was heated to about 75° C.

After the polymerization had started, which was recognizable from an increase in the viscosity, the remaining monomer solution and the remaining initiator solution were added at the same time in the course of 3 and about 6 hours respectively, while the internal temperature was maintained at about 78°-80° C.

On completion of the addition the mixture was postpolymerized at that temperature for approximately one further hour.

EXAMPLES 2 TO 6 AND

Comparative Examples A to C

The method of Example 1 was used to prepare the terpolymers of the present invention in the compositions specified in the table. The comparative substances A to C were prepared as described in reference (2).

Application Testing

The stiffening effect or stiffness was tested using the bending test of Parfums, cosmetiques, aromes no. 89, Octobre-Novembre 1989, 71, which was also presented at the BASF "Cosmeticon" symposium May 10-11, 1990, in Heidelberg. This test provides an indication of the force which is required to bend a strand of hair which has been treated with the film-forming polymer solution until the film breaks. The higher the force required, the higher the stiffness.

The washoff characteristics of polymers on the hair were tested by the following method:

The strands of hair are wetted with a 3% strength by weight ethanolic solution of the polymer and then air dried. Thereafter the strands of hair are moved up and down in a 10% strength by weight aqueous sodium lauryl ether sulfate solution at 35°–40° C. for 30 seconds, the hair being only briefly compressed, to break the polymer film, but not intensively rubbed. The strands of hair are rinsed off with luke warm water and the process of washing with the surface-active solution is repeated once more. Following the final rinse, the hair is pressed off between filter paper and then air dried. The assessment is carried out visually with the hair being twirled to bring any still adhering polymer to light. The assessment scale ranges from "good" via "still acceptable" to "poor".

The table which follows shows in addition to the terpolymer compositions and their K values the results of the bending test and the washoff test and also the water-solubility. The three application tests were each carried out with a 100% neutralized polymer.

from 25 to 65, wherein said terpolymer is water-soluble and said terpolymer is sufficient to form a composition providing a bending force of 104 pounds or greater.

2. A terpolymer as claimed in claim 1, obtainable by free radical polymerization of 10-19% by weight of N-vinylpyrrolidone, 55-74% by weight of tert-butyl acrylate or methacrylate and 16-25% by weight of acrylic or methacrylic acid, whose carboxyl groups have been neutralized with an organic amine, ammonia or a basic alkali metal compound to an extent of from 5 to 100% and which has a K value of from 35 to 55.

3. A hair setting composition, comprising a film forming terpolymer as claimed in claim 1.

4. A hair setting composition, containing from 1 to 15% by weight of a terpolymer as claimed in claim 1, from 10 to 99% by weight of a solvent selected from the group consisting of water, acetone, ethanol, n-propanol, n-butanol, isopropanol, 1-methoxypropanol and mixtures thereof and from 0 to 90% by weight of a propellant selected from the group consisting of propane, n-butane, isobutane, 2,2-dimethylpropane, isopentane, dimethyl ether and mixtures thereof.

5. A method for setting hair, which comprises contacting hair with a film forming terpolymer as claimed in claim 1.

6. A terpolymer as claimed in claim 1, comprising 10-15% by weight N-vinylpyrrolidone.

7. A terpolymer as claimed in claim 1, comprising 16-25% by weight acrylic or methacrylic acid.

8. A terpolymer as claimed in claim 1, comprising 18-25% by weight of acrylic or methacrylic acid.

9. A terpolymer obtained by free radical polymerization of 10-19% by weight of N-vinylpyrrolidone,

| Experiment No. | Composition [% by weight] | | | K value | Bending test [pond] | Washoff characteristics | Solubility in water |
|---|---|---|---|---|---|---|---|
| | VP | tBA | MAA | | | | |
| 1 | 20 | 60 | 20 | 45 | 117 | good | clear solution |
| 2 | 10 | 70 | 20 | 53 | 117 | good | bluish solution |
| 3 | 15 | 69 | 16 | 40 | 111 | good | opaque |
| 4 | 12 | 70 | 18 | 42 | 108 | good | slightly opaque |
| 5 | 19 | 65 | 16 | 38 | 107 | good | cloudy |
| 6 | 20 | 55 | 25 | 40 | 104 | good | clear solution |
| For comparison: | | | | | | | |
| A | 20 | 70 | 10 | 24 | 48 | good | clear solution |
| B | 20 | 70 | 10 | 37 | 92 | poor | cloudy, sediment |
| C | 20 | 70 | 10 | 44 | 106 | poor | cloudy, sediment |

VP: N-Vinylpyrrolidone, tBA: tert-butyl acrylate, MAA: methacrylic acid
The substances of Comparative Examples A to C are in accordance with reference (2).
The terpolymer of Example 1 has a curl retention of 88% and a propane/butane compatibility of 54%
(for comparison, Example A: 90% curl retention and 72% propane/butane compatibility).

We claim:

1. A terpolymer, obtainable by free radical polymerization of 10-19% by weight of N-vinylpyrrolidone, 46-74% by weight of tert-butyl acrylate or methacrylate and 16-30% by weight of acrylic or methacrylic acid, whose carboxyl groups may be partially or completely neutralized with an organic amine, ammonia or a basic metal compound and which has a K value of 46-74% by weight of tert-butyl acrylate or methacrylate, and 16-30% by weight of acrylic or methacrylic acid, whose carboxyl groups may be partially or completely neutralized with an organic amine, ammonia or a basic alkali metal compound and which has a K value of from 38-53.

* * * * *